United States Patent
Chaves Noguera et al.

(10) Patent No.: US 9,804,140 B2
(45) Date of Patent: Oct. 31, 2017

(54) SMART STICKER FOR USE WITH PERISHABLE FOODS

(71) Applicant: Etripes, SA, Heredia (CR)

(72) Inventors: Sindy Johanna Chaves Noguera, Heredia (CR); Juan Scott Chaves Noguera, Heredia (CR)

(*) Notice: Subject to any disclaimer, the term of this patent is extended or adjusted under 35 U.S.C. 154(b) by 294 days.

(21) Appl. No.: 14/862,218

(22) Filed: Sep. 23, 2015

(65) Prior Publication Data

US 2016/0011164 A1  Jan. 14, 2016

Related U.S. Application Data

(63) Continuation-in-part of application No. 14/010,368, filed on Aug. 26, 2013, now abandoned.

(51) Int. Cl.
| | | |
|---|---|---|
| *G01N 31/22* | (2006.01) | |
| *G01N 21/78* | (2006.01) | |
| *G01N 33/12* | (2006.01) | |
| *G01N 33/02* | (2006.01) | |
| *G01N 33/68* | (2006.01) | |
| *G09F 3/10* | (2006.01) | |
| *G01J 1/48* | (2006.01) | |
| *C09D 11/101* | (2014.01) | |

(52) U.S. Cl.
CPC ............ *G01N 33/12* (2013.01); *G01N 21/78* (2013.01); *G01N 31/22* (2013.01); *G01N 33/02* (2013.01); *G01N 33/6803* (2013.01); *A61J 2205/20* (2013.01); *C09D 11/101* (2013.01); *G01N 31/229* (2013.01); *G09F 3/10* (2013.01)

(58) Field of Classification Search
CPC ...... G01N 21/78; G01N 31/229; G01N 33/12; G01N 33/6803; G01N 31/22; G01N 33/02; A61J 2205/20; G09F 3/10; C09D 11/101

See application file for complete search history.

(56) References Cited

U.S. PATENT DOCUMENTS

| | | | |
|---|---|---|---|
| 5,254,473 A | 10/1993 | Patel | |
| 5,750,406 A * | 5/1998 | Nakajima | G01N 1/2273 422/53 |
| 2008/0226834 A1 | 9/2008 | Krohn | |
| 2009/0217863 A1 | 9/2009 | Muskal et al. | |
| 2010/0112680 A1* | 5/2010 | Brockwell | A61B 5/07 435/287.9 |

OTHER PUBLICATIONS

Alexander, D.B. and D.A. Zuberer, Use of chrome azurol S reagents to evaluate siderophore production by rhizosphere bacteria, Biology and Fertility of Soils, 1991, 12:39-45.
Ning, Luo et al., Synthesis and characterization of carbon-encapsulated iron/ironcarbide nanoparticle by detonation method, Elsevier, Jun. 25, 2010.

* cited by examiner

*Primary Examiner* — Jennifer Wecker
(74) *Attorney, Agent, or Firm* — Patrick A. Reid; Larson & Larson, P.A.

(57) ABSTRACT

A smart sticker for determining the current state of raw meat for safe human consumption is provided. The smart sticker indicates the quality or decomposition of the meat by changing color. The smart sticker employs a cupric nitrate solution mixed with a polymeric silicon substrate that forms a complex with the valence electrons on the nitrogen atom of an amino acid residue. After this interaction occurs, the smart sticker changes color from, for example, light blue to purple.

19 Claims, 1 Drawing Sheet

SMART STICKER FOR USE WITH PERISHABLE FOODS

CROSS-REFERENCE TO RELATED APPLICATION

This application is a non-provisional application that is a continuation-in-part of U.S. patent application Ser. No. 14/010,368 titled Nanotechnology Smart Sticker for Use with Perishable Foods, filed Aug. 26, 2013.

FIELD

The present invention relates to smart stickers for use with perishable foods to indicate freshness and the presence of harmful bacteria.

BACKGROUND

Each year, millions of people around the world are sickened by bacterial food poisoning. This is largely due to the consumer being unaware that he is consuming a food tainted with harmful bacteria. Rampant food poisoning from harmful bacteria is widespread and is occurring with alarming frequency. Bacteria such as *Salmonella, Escherichia coli* (also known as *E. coli*), as well as the larger genus bacteria *Campylobacter*, which includes *E. Coli*, are appearing in foods and making people sick around the world. The sickness manifests as gastrointestinal flu, septicemia, and even death in some cases from a severe bacterial infection.

Sell by dates and expirations dates are two commonly used systems to indicate food freshness. But both are inadequate in today's world where products are shipped all over the world by trains, trucks, ships, and planes.

It is generally known that changes in temperatures can harm perishable foods, especially meat products. These temperature changes can result in sickness, and sometimes death caused by the bacterial growth that occurs during these fluctuations in temperature. But merely detecting changes in temperature is insufficient to guarantee detection of food spoilage.

Accordingly, what is needed is an improved smart sticker that can be applied directly to raw meat of all types and is safe for use at every point in the chain of food commerce.

SUMMARY

Disclosed within is improved smart sticker for determining the state of decomposition of meat. The smart sticker can detect decomposition of meat that has been stored for too long regardless of whether that meat has been stored in the freezer or at room temperature. The smart sticker can detect decomposition of meat caused by aerobic or anaerobic processes, or due to a microorganism or bacteria present in the meat. The smart sticker accomplishes these functions by detecting denatured proteins. The smart sticker then provides feedback to a user by changing color in a particular area of the sticker.

In this application the deterioration of the meat is measured by detection of biogenic amines and alcohols. The result of the measurement is shown using an easy-to-handle colorimetric substrate. The colorimetric substrate detects these amino groups on the products formed during the denaturation of proteins in which higher-order structures are broken due to microbial attack, natural degradation, or fermentation.

By way of background, proteins exist in nature in a variety of sequences and three-dimensional structures. These sequences and structures are called primary, secondary, tertiary, and quaternary. Primary structure is the sequence of amino acids that make up a single protein chain. Secondary structure describes the structure of localized segments of a single protein chain that has folded onto itself through additional interactions between nearby amino acids that make up the primary chain. Tertiary structure describes the geometric shape of a single protein chain when a portion of secondary structure interacts or folds with other primary or secondary portions of the chain. Quaternary structure is used to describe the interactions between two or more protein chains.

The smart sticker utilizes the structures of proteins to determine the level of decomposition. The sticker has in its composition a compound capable of forming a coordination complex with the valence electrons of the nitrogen of an amino acid residue. Due to the specific interaction with the valence electron group of the nitrogen, the sticker only detects the amino group when it becomes degraded and has lost its quaternary or tertiary structure. When the food is fresh, meaning the proteins have not decomposed and retain all three-dimensional networks, the valence electrons on the nitrogen atom will be shielded from interacting with the smart sticker due to the three-dimensional structure of the proteins.

For the reaction to occur properly and for the apparatus to react properly to the reaction, a mild base catalyst is required. The catalyst generates an alkaline medium in which the reaction occurs.

This device detects a change in electrical conductivity due to the available electrons present as the proteins degrade and alcohols start to form due to the fermentation process that most microorganisms are able to carry out.

The creation of the smart sticker involves combining the additive with a polymeric substrate containing silicon. The additive is a solution of cupric nitrate combined with a mild base and salt mix. The user of the device only has to take a small sample of the meat, place the meat on the device, and wait approximately 5-10 minutes for the reaction to occur. If the reaction is positive, the substrate will change from light blue to purple, indicating that it detected a high percentage of electrons due to the decomposition of the three-dimensional structure of the proteins.

Alcohols are also released during the decomposition process. The smart sticker detects the valence electron pairs that exist on the oxygen atom of the alcohol group.

The intensity of the color produced in the substrate is proportional to the number of peptide bonds that have been broken. Furthermore, the speed of the color change is proportional to the number of peptide bonds that have been broken.

The number of secreted molecules is directly proportional to the number of valence electrons that are exposed. Once this interaction occurs, the ink changes color, for example, from blue to purple.

It should be further noted that the disclosed smart sticker is usable with many perishable foods. As long as the food contains protein, the smart sticker can be used to determine the amount of decay of that food product.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
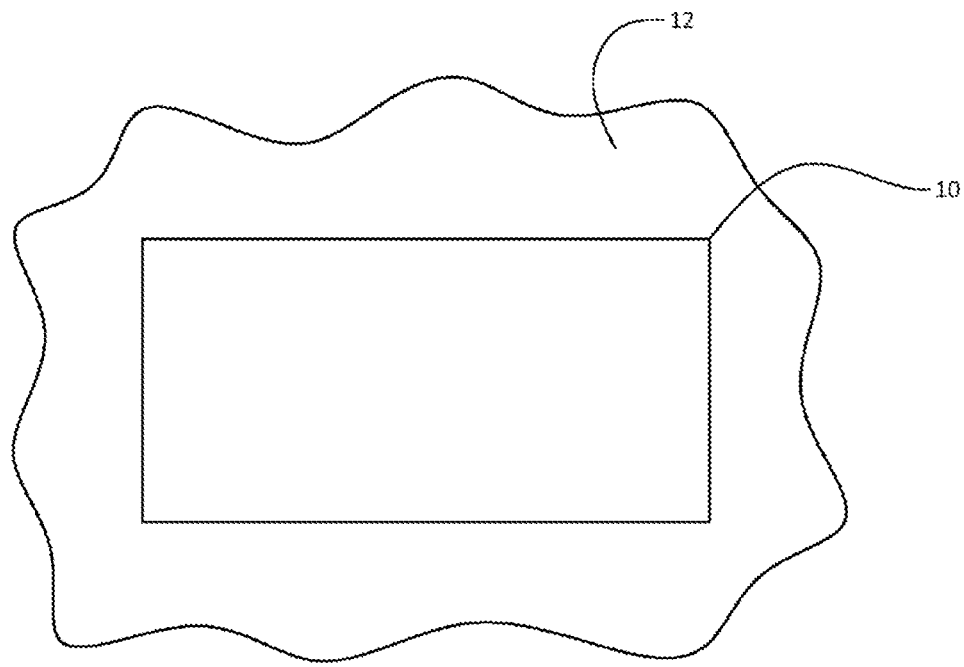
FIG. 1 is a perspective view of a piece of raw meat with the smart sticker of the present invention applied thereupon.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a smart sticker 10 of the present invention is shown applied to a piece of raw meat 12. Sticker 10 includes an additive. The additive is a solution of cupric nitrate combined with a mild base (e.g., aqueous ammonia) and a salt.

The smart sticker has two fundamental parts: the additive that contains the compounds that help visualize the reaction, and the silicon substrate. The silicon substrate supports and controls the viscosity of the additive.

The device is safe to use under refrigeration, as humidity does not affect its efficiency. It is preferable to store the device in the refrigerator for the detection because the additive achieves optimum cohesion at lower temperatures.

Preferably, a substrate of 3 mm thick is used because the color variation between the initial state and the final state is clearer than when used with thinner substrates. Increasing the thickness of the substrate creates the clearer image because a larger quantity of additive will be contained in the smart sticker. This allows for more cupric nitrate ions to complex with valence electron pairs.

The disclosed invention is intended for use detecting decomposition of meat from day one of spoilage to day five. The device continues to detect decomposition of meat after five days, but after five days a consumer is likely to detect spoilage without the aid of the invention.

Figure 2:
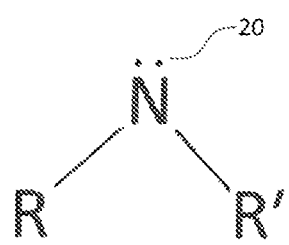
FIG. 2 illustrates the valence electron pair of the nitrogen atom in an amino acid residue that becomes exposed when the protein denatures.

Referring to FIG. 2, the valence electron pair 20 on the nitrogen atom is detected by the additive. The cupric nitrate in the additive forms a complex with the valence electrons. As the cupric nitrate complexes with the electrons, the smart sticker changes color.

The change in color of sticker 10 can be observed with the naked eye. Additional pairs of exposed electrons will result in a deeper and faster color change. By observing the change in color of the sticker, one can easily identify the level of decomposition of the food. Therefore, the color change of the sticker 10 is directly proportional to the number of exposed electron pairs detected by the additive.

In the presently described embodiment, the change in color is from light blue to purple. However, nothing requires that the change of color be regulated to just blue to purple. Any other changing color combination can be employed.

Now turning to a method for using the disclosed smart sticker.

First, one must create the cupric nitrate solution. There are a variety of known chemical reactions that create an aqueous cupric nitrate solution.

Second, add a mild base, such as ammonia, to the cupric nitrate solution. The addition of the mild base helps to catalyze the reaction between the cupric nitrate and the valence electron pairs on the decomposed proteins.

Third, mix the cupric nitrate and mild base solution with a polymeric silicon substrate. The silicon substrate aids in creating a solid smart sticker.

Fourth, form the silicon substrate and additive mixture into the smart sticker. Because the silicon substrate provides higher viscosity to the mixture, it is possible to cool the mixture and form it into stickers.

Fifth, apply the smart sticker directly to a piece of food. As soon as the smart sticker is in contact with the food, the cupric nitrate ions will begin complexing with the valence electrons present in the proteins.

Sixth, the cupric nitrate additive will begin complexing with any exposed valence electron pairs. Denatured proteins will have valence electrons exposed on the nitrogen atom. Also, certain decomposition reactions also create biogenic alcohol byproducts. The oxygen atoms of those alcohols will have valence electrons with which the cupric nitrate will react. Thus, the reaction can detect decomposition by natural causes or bacterial causes.

Finally, wait enough time to determine the amount of spoilage of the food Preferably 5 to 10 minutes.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A smart sticker used to detect meat decomposition caused by a regular spoliation process, the smart sticker comprising:
   a. an additive containing cupric nitrate;
   b. a polymeric silicon substrate;
   c. a solid state sticker formed by the combination of the additive and the polymeric silicon substrate;
   d. wherein the smart sticker is configured to change color by a reaction occurring between a valence electron pair and cupric nitrate ions, thereby indicating decomposition of a protein.

2. The smart sticker of claim 1, wherein the smart sticker changes color when it detects the valence electrons on a nitrogen atom of an amino acid residue after the three-dimensional structures of proteins break down.

3. The smart sticker of claim 1, wherein the smart sticker is at least three millimeters thick.

4. The smart sticker of claim 1, wherein the additive is a solution of cupric nitrate mixed with a mild base and a salt.

5. The smart sticker of claim 1, wherein the color change occurs as a result of electron flow.

6. The smart sticker of claim 1, wherein the smart sticker detects valence electron pairs on biogenic amines and alcohols that are produced by the decomposition of food.

7. The smart sticker of claim 1, wherein the color-change is from light blue to purple.

8. A smart sticker applied directly to the surface of raw food, the smart sticker comprising:
   a. a substrate, the substrate containing a polymeric silicon;
   b. an additive, the additive containing a cupric nitrate solution and a mild base; and
   c. the smart sticker is formed into a solid state wafer by mixing the additive with the substrate, wherein the smart sticker is configured to indicate deterioration of raw food by a complexing reaction with valence electron pairs on an amino acid residue of a protein.

9. The smart sticker of claim 8, wherein the reaction is between a valence electron pair exposed in denatured protein and a molecule of cupric nitrate.

10. The smart sticker of claim 9, wherein the valence electron pair is located on a nitrogen atom of an amino acid residue.

11. The smart sticker of claim 9, wherein the valence electron pair is located on an oxygen atom of a biogenic alcohol byproduct of decomposition.

12. The smart sticker of claim 8, wherein the color-change is from light blue to purple.

13. The smart sticker of claim 8, wherein the smart sticker detects denatured proteins in meat, fruits, vegetables, cheese and other dairy products, and bread products.

14. A method of detecting spoilage of meat and poultry, the method comprising the steps of:
   a. creating an aqueous cupric nitrate solution;
   b. adding a mild base to the cupric nitrate solution;
   c. mixing the cupric nitrate solution and the mild base with a polymeric silicon substrate;
   d. forming a mixture containing the cupric nitrate solution, the mild base, and the polymeric silicon substrate into a smart sticker;
   e. applying a smart sticker the surface of a piece of food;
   f. complexing the cupric nitrate solution with a valence electron pair on byproducts of food decomposition;
   g. waiting for the cupric nitrate additive to complex with enough valence electron pairs to change the color of the smart sticker.

15. The method of claim 14, wherein the piece of food is selected from the group consisting of: meat, poultry, fish, vegetables, and cheese.

16. The method of claim 14, wherein step c further comprises waiting between 5 and 10 minutes.

17. The method of claim 14, wherein the smart sticker of step d is formed by creating a plurality of smart sticker patches and letting the plurality of smart sticker patches solidify.

18. The method of claim 14, wherein the valence electron pairs in step f are on the nitrogen atom of an amino acid residue or on the oxygen atom of alcohols, both of which are exposed during the decomposition of proteins.

19. The method of claim 14, wherein the color change of the smart sticker is from light blue to purple.

* * * * *